(12) United States Patent
Collin et al.

(10) Patent No.: US 11,358,967 B2
(45) Date of Patent: Jun. 14, 2022

(54) SUBSTITUTED PYRAZINO[2,3-B]PYRAZINES AND PYRAZINO[2,3-C]PYRIDAZINES AS MODULATORS OF ROR GAMMA

(71) Applicant: Boehringer Ingelheim International GmbH, Ingelheim am Rhein (DE)

(72) Inventors: Delphine Collin, New Milford, CT (US); Johanna Csengery, New Fairfield, CT (US); Robert Owen Hughes, Newtown, CT (US); Michael Robert Turner, Danbury, CT (US); Lifen Wu, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 794 days.

(21) Appl. No.: 16/071,147

(22) PCT Filed: Jan. 18, 2017

(86) PCT No.: PCT/US2017/013841
§ 371 (c)(1),
(2) Date: Jul. 19, 2018

(87) PCT Pub. No.: WO2017/127375
PCT Pub. Date: Jul. 27, 2017

(65) Prior Publication Data
US 2021/0171527 A1 Jun. 10, 2021

Related U.S. Application Data

(60) Provisional application No. 62/280,746, filed on Jan. 20, 2016.

(51) Int. Cl.
| A61K 31/4985 | (2006.01) |
| C07D 487/04 | (2006.01) |
| A61P 37/06 | (2006.01) |

(52) U.S. Cl.
CPC ............ *C07D 487/04* (2013.01); *A61P 37/06* (2018.01)

(58) Field of Classification Search
CPC .......................... A61K 31/4985; C07D 487/04

USPC .......................................... 514/249; 544/350
See application file for complete search history.

(56) References Cited

U.S. PATENT DOCUMENTS

| 2015/0291607 A1 | 10/2015 | Bakonyi et al. |
| 2016/0075706 A1 | 3/2016 | Bakonyi et al. |
| 2016/0159791 A1 | 6/2016 | Cook et al. |
| 2016/0251310 A1 | 9/2016 | Cook et al. |
| 2017/0008894 A1 | 1/2017 | Bakonyi et al. |

FOREIGN PATENT DOCUMENTS

| WO | 2013169704 A2 | 11/2013 | |
| WO | 2015017335 A1 | 2/2015 | |
| WO | 2015035032 A1 | 3/2015 | |
| WO | 2015160654 A1 | 10/2015 | |
| WO | WO-2017127375 A1 * | 7/2017 | ............. A61P 11/02 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion for corresponding application, PCT/US2017/013841, dated Feb. 28, 2017.

* cited by examiner

*Primary Examiner* — Douglas M Willis
(74) *Attorney, Agent, or Firm* — Philip I. Datlow

(57) ABSTRACT

The present invention encompasses compounds of the formula (I), wherein the variables are defined herein which are suitable for the modulation of RORγ and the treatment of diseases related to the modulation of RORγ. The present invention also encompasses processes of making compounds of formula (I) and pharmaceutical preparations containing them.

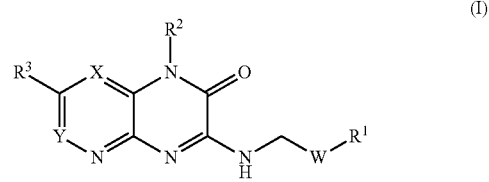

10 Claims, No Drawings

SUBSTITUTED PYRAZINO[2,3-B]PYRAZINES AND PYRAZINO[2,3-C]PYRIDAZINES AS MODULATORS OF ROR GAMMA

BACKGROUND OF THE INVENTION

Technical Field

The present invention relates to novel compounds which modulate the activity of RORγ and their use as medicaments.

Background

RORγ (retinoic acid receptor related orphan receptor gamma) (also referred to as "RORγt") is a transcription factor belonging to the steroid hormone receptor superfamily (reviewed in Jetten 2006. Adv. Dev Biol. 16: 313-355). RORγ has been identified as a transcriptional factor that is required for the differentiation of T cells and secretion of Interleukin 17 (IL-17) from a subset of T cells termed $Th_{17}$ cells (Ivanov, Cell 2006, 126, 1121-1133). The rationale for the use of a RORγ targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with neutralizing antibodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated $Th_{17}$ T cells via inhibition of RORγ may offer similar therapeutic benefit.

SUMMARY OF THE INVENTION

The invention comprises a novel class of heteroaromatic compounds and methods for making and using the same, said compounds having the general structure of formula (I), wherein the substituent groups are as herein defined:

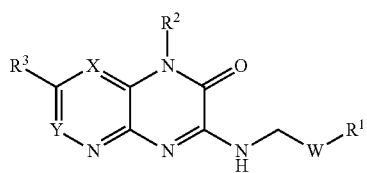

These compounds are useful for the treatment of autoimmune and allergic disorders in that they exhibit potent inhibitory activity against RORγ.

In a further aspect, a goal of the present invention is to provide compounds with metabolic stability properties consistent with acceptable pharmacokinetic properties. As is known in the art, compounds having poor metabolic stability may not readily achieve desirable therapeutic levels. The preferred compounds of the present invention would be expected to have metabolic stability properties consistent with being a suitable drug.

DETAILED DESCRIPTION OF THE INVENTION

Definitions and Conventions Used

Terms that are not specifically defined here have the meanings that would be apparent to a person skilled in the art, in light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x number of carbon atoms.

In general, for groups comprising two or more subgroups, unless otherwise indicated the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached. However, if a bond is depicted just prior to the first named subgroup, then that first named subgroup is the radical attachment point, for example, the substituent "—S(O)$_n$C$_{1-6}$alkyl" means a $C_{1-6}$-alkyl-group which is bound to an S(O)$_n$ group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$) CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$),1-pentyl n-pentyl; —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 2,2-dimethyl-1-propyl(neo-pentyl; —CH$_2$C (CH$_3$)$_3$),2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$CH$_2$ CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$ alkylamino or $C_{x-y}$ alkoxy.

Unlike alkyl, alkenyl, when used alone or in combination, consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed. Alkenyl may optionally be present in the cis or trans or E or Z orientation with regard to the double bond(s).

Unlike alkyl, alkynyl, when used alone or in combination, consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl), when used alone or in combination, is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —C≡C—CF$_3$, —CHFCH$_2$CH$_3$, —CHFCH$_2$CF$_3$ etc.

Halogen relates to fluorine, chlorine, bromine and/or iodine atoms.

The term "cycloalkyl", when used alone or in combination, refers to a nonaromatic 3 to 12-membered (but preferably, 3 to 6-membered) monocyclic carbocyclic radical or a nonaromatic 6 to 10-membered fused bicyclic, bridged bicyclic, propellane or spirocyclic carbocyclic radical. The $C_{3-12}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[1.1.1]pentane, bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered propellane carbocyclic radicals include but are not limited to [1.1.11]propellane, [3.3.3]propellane and [3.3.1]propellane. Non-limiting examples of 6 to 10-membered spirocyclic carbocyclic radicals include but are not limited to spiro[3.3]heptanyl, spiro[3,4]octanyl and spiro[4,4]heptanyl.

The term "heterocyclyl", when used alone or in combination, refers to a heterocyclic ring system that contains 2-10 carbon atoms and one to four heteroatom ring atoms chosen from NH, NR', oxygen and sulfur wherein R' is $C_{1-6}$ alkyl. The term "heterocyclyl" includes stable nonaromatic 4-8 membered monocyclic heterocyclic radicals or a stable nonaromatic 6 to 11-membered fused bicyclic, bridged bicyclic or spirocyclic heterocyclic radical. The heterocycle may be either completely saturated or partially unsaturated. In one embodiment the heterocycle is a $C_{3-6}$ heterocycle, i.e., containing 3 to 6 ring carbon atoms. Non-limiting examples of nonaromatic monocyclic heterocyclic radicals include tetrahydrofuranyl, azetidinyl, pyrrolidinyl, pyranyl, tetrahydropyranyl, dioxanyl, thiomorpholinyl, 1,1-dioxo-1.lamda$_6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. Sulfur and nitrogen may optionally be present in all the possible oxidation stages (for example, sulfur: sulfoxide —SO—, sulfone —SO$_2$—; nitrogen: N-oxide).

The term "aryl", when used alone or in combination, refers to an aromatic hydrocarbon ring containing from six to fourteen carbon ring atoms (e.g., a $C_{6-14}$ aryl, preferably $C_{6-10}$ aryl). The term $C_{6-14}$ aryl includes monocyclic rings, fused rings and bicyclic rings where at least one of the rings is aromatic. Non-limiting examples of $C_{6-14}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "heteroaryl", when used alone or in combination, refers to a heteroaromatic ring system that contains 2-10 carbon atoms and 1-4 heteroatom ring atoms selected from N, NH, NR', O and S wherein R' is $C_{1-6}$ alkyl. The term "heteroaryl" includes aromatic 5 to 6-membered monocyclic heteroaryls and aromatic 7 to 11-membered heteroaryl bicyclic or fused rings where at least one of the rings is aromatic. Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic or fused rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl. Sulfur and nitrogen may optionally be present in all the possible oxidation stages (for example, sulphur: sulfoxide —SO—, sulfone —SO$_2$—; nitrogen: N-oxide).

The compounds of the invention are only those which are contemplated to be chemically stable as will be appreciated by those skilled in the art. For example, a compound which would have a "dangling valency", or a carbanion are not compounds contemplated by the inventive methods disclosed herein.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and their corresponding unsolvated as well as solvated forms with pharmaceutically acceptable solvents such as water, ethanol and the like.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$ $^{14}C$ $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio. Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

By a therapeutically effective amount for the purposes of this invention is meant a quantity of substance that is capable of obviating symptoms of illness or alleviating these symptoms, or which prolong the survival of a treated patient.

Embodiments of the Invention

A general embodiment of the invention is directed to a compound of formula (I) below:

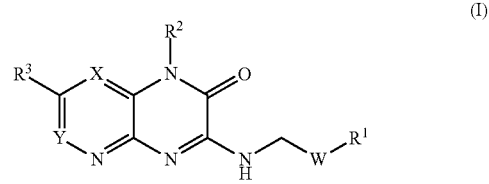

(I)

wherein:

X is N and Y is C; or

X is C and Y is N;

W is selected from pyridinyl, pyrimidinyl, pyrizinyl and phenyl;

$R^1$ is selected from $-S(O)_nR^7$, $-S(O)_nNR^8R^9$, and $-S(O)(NH)R^7$; wherein $R^7$ is $C_{1-3}$ alkyl $R^8$ and $R^9$ are each $-H$; and n is 1 or 2;

$R^2$ is $C_{1-6}$alkyl, optionally substituted with one or two groups independently selected from $C_{3-6}$cycloalkyl, halogen, $-CF_3$ and $-CN$;

$R^3$ is selected from

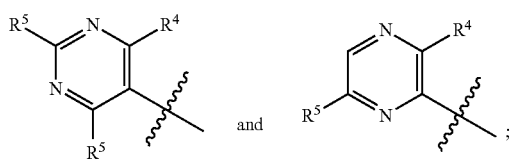

$R^4$ and $R^5$ are independently selected from $C_{1-3}$alkyl, cyclopropyl and methoxy;

$R^6$ is selected from H, $-NH_2$, $C_{1-3}$alkyl, cyclopropyl and methoxy;

and the pharmaceutically acceptable salts thereof.

In another embodiment, there are provided compounds of the formula (I) as described according to the embodiment above and wherein X is N and Y is C; or X is C and Y is N;

W is selected from 2-pyridinyl, 3-pyridinyl, 2-pyrimidinyl and phenyl;

$R^1$ is selected from $-S(O)_nR^7$; wherein $R^7$ is $C_{1-3}$ alkyl and n is 2;

$R^2$ is $C_{1-6}$alkyl, optionally substituted with one or two groups independently selected from cyclopropyl, $-CF_3$ and $-CN$;

R³ is selected from

[chemical structure: pyrimidine with R⁵, R⁴, R⁵ substituents] and [chemical structure: pyrazine with R⁴, R⁵ substituents];

R⁴ and R⁵ are independently selected from $C_{1-3}$alkyl, cyclopropyl and methoxy;

R⁶ is selected from H and —NH₂;

and the pharmaceutically acceptable salts thereof.

In another embodiment, there are provided compounds of the formula (I) as described according to any of the embodiments above and wherein X is N and Y is C;

and the pharmaceutically acceptable salts thereof.

In another embodiment, there are provided compounds of the formula (I) as described according to any of the embodiments above and wherein X is C and Y is N;

and the pharmaceutically acceptable salts thereof.

In another embodiment, there are provided compounds of the formula (I) as described in any of the embodiments above and wherein R³ is

[chemical structure: pyrimidine with R⁵, R⁴, R⁵ substituents];

and the pharmaceutically acceptable salts thereof.

In another embodiment, there are provided compounds of the formula (I) as described in any of the embodiments above and wherein X is N and Y is C;

W is 2-pyridinyl or 3-pyridinyl;

R¹ is selected from —S(O)$_n$R⁷; wherein R⁷ is $C_{1-3}$ alkyl and n is 2;

R² is $C_{1-5}$alkyl, optionally substituted cyclopropyl;

R³ is

[chemical structure: pyrimidine with R⁵, R⁴, R⁵ substituents];

R⁴ and R⁵ are independently selected from $C_{1-3}$alkyl, cyclopropyl and methoxy;

R⁶ is H;

and the pharmaceutically acceptable salts thereof.

Table 1 shows representative compounds of the invention which can be made by the methods described in the general synthetic schemes, the examples, and known methods in the art.

TABLE 1

| Example | Structure | RT | m/z [M + H]⁺ | HPLC Method |
|---|---|---|---|---|
| 1 | [chemical structure] | 1.10 | 565.1 | A |
| 2 | [chemical structure] | 0.97 | 537.4 | A |

TABLE 1-continued

| Example | Structure | RT | m/z [M + H]+ | HPLC Method |
|---|---|---|---|---|
| 3 | 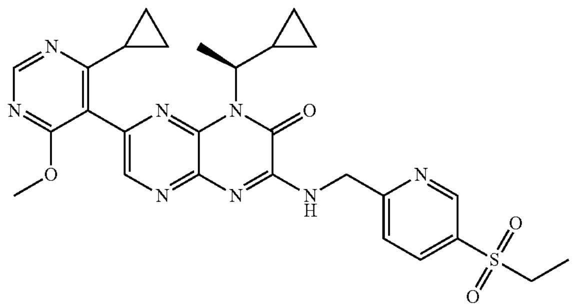 [SMILES: CCS(=O)(=O)c1ccc(CNc2nc3ncc(-c4c(OC)ncnc4C4CC4)nc3n([C@@H](C)C3CC3)c2=O)nc1] | 2.43 | 563.3 | B |
| 4 | 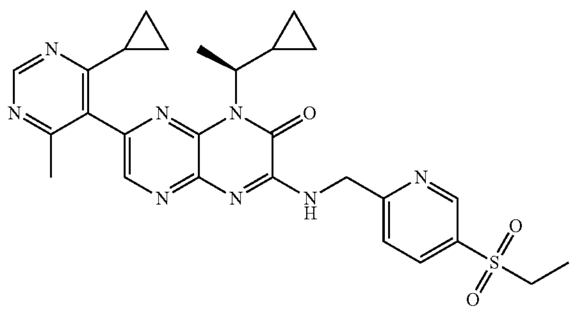 [SMILES: CCS(=O)(=O)c1ccc(CNc2nc3ncc(-c4c(C)ncnc4C4CC4)nc3n([C@@H](C)C3CC3)c2=O)nc1] | 2.13 | 547.3 | B |
| 5 | 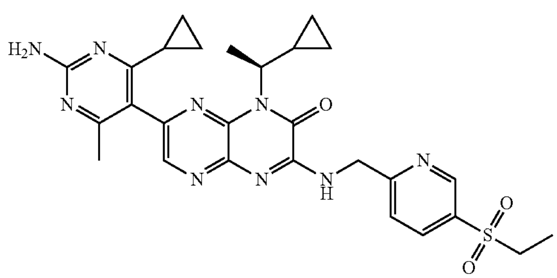 [SMILES: CCS(=O)(=O)c1ccc(CNc2nc3ncc(-c4c(C)nc(N)nc4C4CC4)nc3n([C@@H](C)C3CC3)c2=O)nc1] | 1.45 | 562.5 | B |
| 6 | 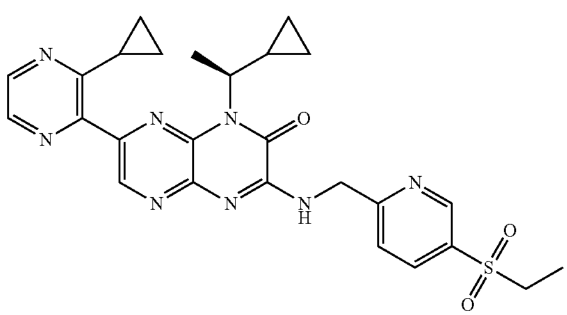 [SMILES: CCS(=O)(=O)c1ccc(CNc2nc3ncc(-c4nccnc4C4CC4)nc3n([C@@H](C)C3CC3)c2=O)nc1] | 2.51 | 533.0 | B |
| 7 | 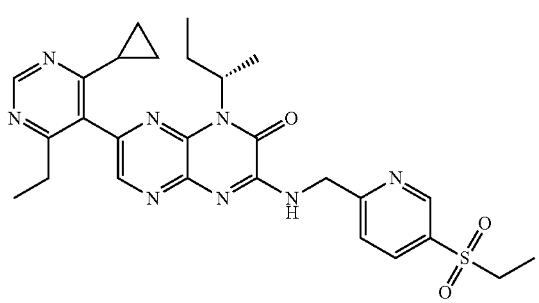 [SMILES: CCc1ncnc(C2CC2)c1-c1cnc2nc(NCc3ccc(S(=O)(=O)CC)cn3)c(=O)n([C@@H](C)CC)c2n1] | 2.34 | 551.5 | B |

TABLE 1-continued

| Example | Structure | RT | m/z [M + H]+ | HPLC Method |
|---|---|---|---|---|
| 8 | 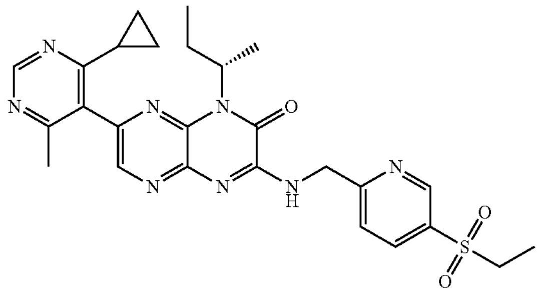 [SMILES: CC[C@H](C)n1c(=O)c(NCc2ccc(S(=O)(=O)CC)cn2)nc2ncc(-c3c(C)ncnc3C3CC3)nc21] | 2.05 | 535.5 | B |
| 9 | 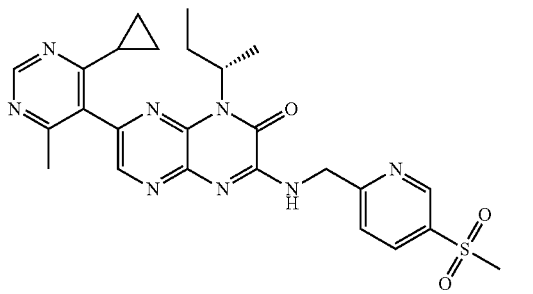 [SMILES: CC[C@H](C)n1c(=O)c(NCc2ccc(S(C)(=O)=O)cn2)nc2ncc(-c3c(C)ncnc3C3CC3)nc21] | 1.91 | 521.5 | B |
| 10 | 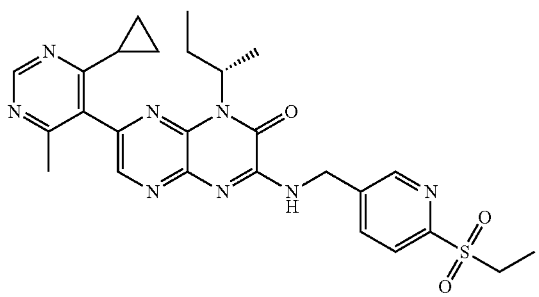 [SMILES: CC[C@H](C)n1c(=O)c(NCc2ccc(S(=O)(=O)CC)nc2)nc2ncc(-c3c(C)ncnc3C3CC3)nc21] | 2.00 | 535.3 | B |
| 11 | 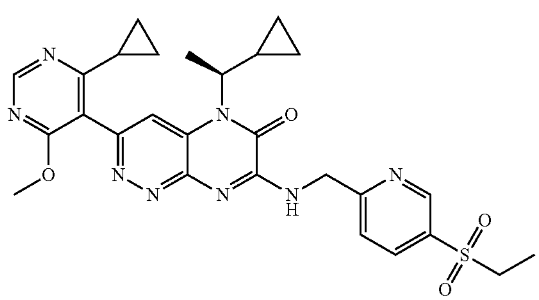 [SMILES: CCS(=O)(=O)c1ccc(CNc2nc3nnc(-c4c(OC)ncnc4C4CC4)cc3n([C@@H](C)C3CC3)c2=O)nc1] | 1.77 | 563.4 | B |
| 12 | 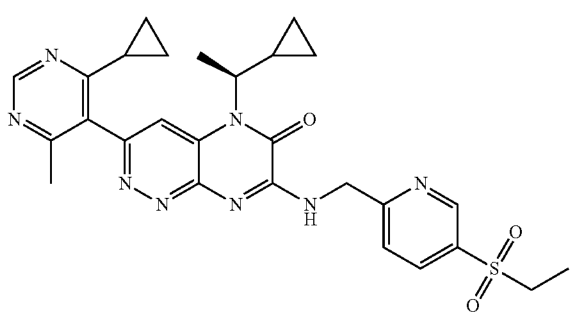 [SMILES: CCS(=O)(=O)c1ccc(CNc2nc3nnc(-c4c(C)ncnc4C4CC4)cc3n([C@@H](C)C3CC3)c2=O)nc1] | 1.56 | 547.5 | B |

In one embodiment, the invention relates to a compound selected from the group consisting of compounds 1-12 depicted in Table 1 above and the pharmaceutically acceptable salts thereof.

The present invention further relates to a pharmaceutically acceptable salt of a compound of the formula (I) with inorganic or organic acids or bases.

In another aspect, the invention relates to compounds of formula (I) or the pharmaceutically acceptable salts thereof as medicaments.

In another aspect, the invention relates to compounds of formula (I) or the pharmaceutically acceptable salts thereof for use in a method for treatment of a patient.

In another aspect, the invention relates to compounds of formula (I) or the pharmaceutically acceptable salts thereof for use in the treatment of autoimmune diseases and allergic disorders.

In another aspect, the invention relates to the use of compounds of formula (I) or the pharmaceutically acceptable salts thereof for preparing a pharmaceutical composition for the treatment of autoimmune diseases and allergic disorders.

In another aspect, the invention relates to a method for the treatment of autoimmune diseases and allergic disorders comprising administering a therapeutically effective amount of a compound of formula (I) or one of the pharmaceutically acceptable salts thereof to a patient.

In another aspect, the invention relates to a pharmaceutical composition containing as active substance one or more compounds of formula (I) or the pharmaceutically acceptable salts thereof optionally in combination with conventional excipients and/or carriers.

The compounds of formula (I) may be made using the general synthetic methods described below, which also constitute part of the invention.

General Synthetic Methods

The compounds according to the invention may be prepared by the methods of synthesis and synthetic examples below, methods known to those of ordinary skill in the art and methods reported in the chemical literature. In the methods of synthesis and examples described hereinafter, the substituents $R^1$, $R^2$, $R^3$, X, Y and W shall have the meanings defined hereinbefore in the detailed description of the compounds of formula I. The methods that are described here are intended as an illustration and for the enablement of the instant invention without restricting the scope of its subject matter, the claimed compounds, and the examples. Where the preparation of starting compounds is not described, they are commercially obtainable, may be prepared analogously to compounds or methods described herein, or are described in the chemical literature. Unless otherwise specified, solvents, temperatures, pressures, and other reaction conditions may be readily selected by one of ordinary skill in the art.

Synthetic Examples

Non-limiting examples demonstrating the preparation of the compounds of the invention are provided below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RP-HPLC). Discrete enantiomers may be obtained by resolution of racemic products using chiral HPLC. RP-HPLC purification methods used anywhere from 0-100% acetonitrile in water containing 0.1% formic acid or 0.1% TFA and used one of the following columns:

a) Waters Sunfire OBD C18 5 μM 30×150 mm column
b) Waters XBridge OBD C18 5 μM 30×150 mm column
c) Waters ODB C8 5 μM 19×150 mm column
d) Waters Atlantis ODB C18 5 μM 19×50 mm column
e) Waters Atlantis T3 OBD 5 μM 30×100 mm column
f) Phenomenex Gemini Axia C18 5 μM 30×100 mm column UPLC/MS Methods:
Analytical UPLC/MS Analysis Method A:
Column: Waters CSH 2.1×50 mm C18 1.7 um column
Gradient:

| Time(min) | 0.05% Formic Acid in Water | 0.05% Formic Acid in ACN | Flow(mL/min) |
|---|---|---|---|
| 0 | 90 | 10 | 0.8 |
| 1.19 | 0 | 100 | 0.8 |
| 1.77 | 0 | 100 | 0.8 |

Analytical LC/MS Analysis Method B:
Column: Waters BEH 2.1×50 mm C18 1.7 um column
Gradient:

| Time(min) | 0.05% Formic Acid in Water | 0.05% Formic Acid in ACN | Flow(mL/min) |
|---|---|---|---|
| 0 | 90 | 10 | 0.8 |
| 4.45 | 0 | 100 | 0.8 |
| 4.58 | 0 | 100 | 0.8 |

LIST OF ABBREVIATIONS USED IN SYNTHETIC EXAMPLES

| | |
|---|---|
| Ac | Acetyl |
| ACN | Acetonitrile |
| AcOH | Acetic acid |
| aq | Aqueous |
| Bu | Butyl |
| Boc$_2$O | Di-tert-butyl dicarbonate |
| DCM | Dichloromethane |
| DIEA | N,N-diisopropylethylamine |
| DMAP | 4-Dimethylaminopyridine |
| DMF | N,N-Dimethylformamide |
| dppf | 1.1'-bis(diphenylphosphino)ferrocene |
| ES+ | Electron spray positive ionization |
| Et | Ethyl |
| EtOAc | Ethyl acetate |
| EtOH | Ethanol |
| h | hour(s) |
| HPLC | High performance liquid chromatography |
| i | Iso |
| LC | Liquid chromatography |
| Me | Methyl |
| MeOH | Methanol |
| min | Minutes |
| MS | Mass spectrometry |
| NMP | N-Methylpyrrolidinone |
| Pd/C | Palladium on carbon |
| Ph | Phenyl |
| PPh3 | Triphenylphosphine |
| Pr | Propyl |
| RaNi | Raney Nickel |
| RT | Retention time (HPLC) |
| rt | Ambient temperature |
| T | Tertiary |
| Tert | Tertiary |

| | |
|---|---|
| Tf | Triflate |
| TEA | Triethylamine |
| TFA | Trifluoroacetic acid |
| THF | Tetrahydrofuran |
| UPLC | Ultra Performance Liquid Chromatography |

Method 1:
Synthesis of Intermediate A

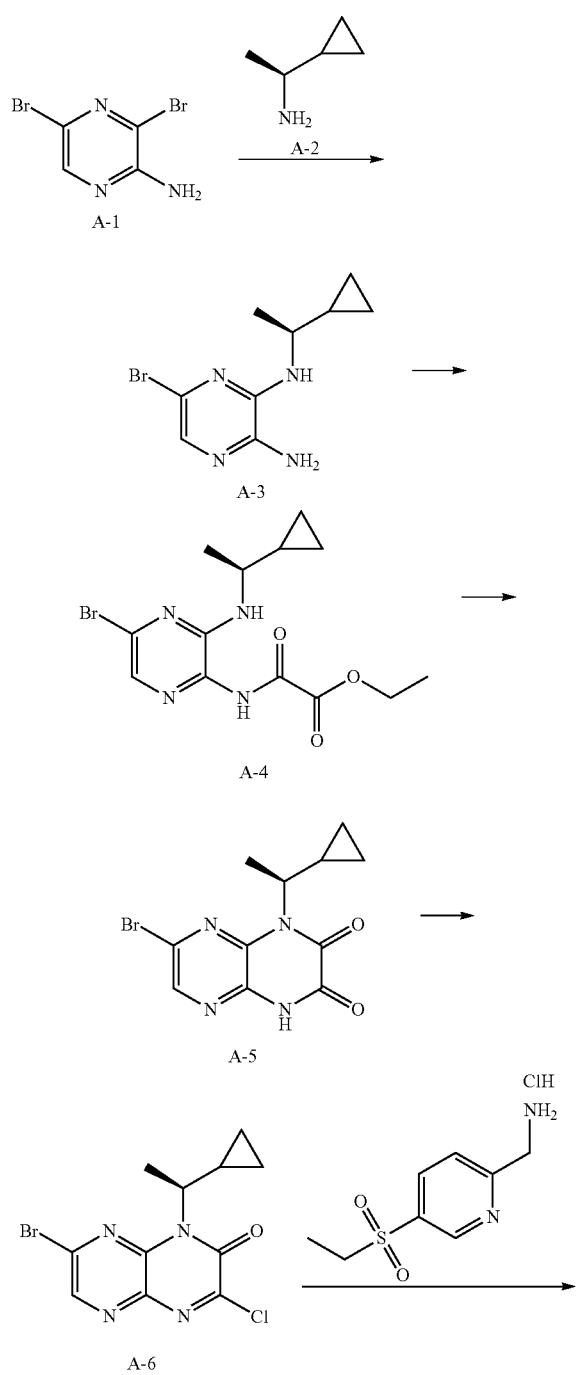

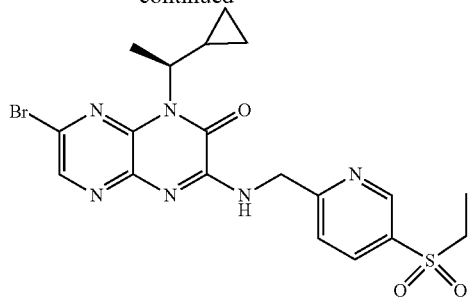

To the solution of A-1 (6 g, 23.73 mmol) in water (60 mL) was added A-2 (4.04 g, 47.45 mmol) and K$_2$CO$_3$ (6.55 g; 47.45 mmol) in a sealed tube. The reaction is stirred at 120° C. for 12 h. At the end of the reaction, the mixture is extracted with EtOAc. The organic layer is dried over Na$_2$SO$_4$ and concentrated. The residue is purified by SiO$_2$ flash chromatography to yield A-3.

To the solution of A-3 (3 g, 11.67 mmol) and K$_2$CO$_3$ (4.35 g; 31.5 mmol) in acetone (25 mL) is added chloro-oxo-acetic acid ethyl ester (4.78 g; 35 mmol) dropwise at 0° C. The mixture is stirred at r.t. for 16 h. At the end of the reaction, the solvent is removed under vacuum to yield crude A-4 which is used directly in the next step.

To the solution of A-4 (3 g, 5.88 mmol) in MeOH (25 mL) is added NaOMe in MeOH (3.18 g, 17.64 mmol). The reaction is stirred at r.t. for 15 h, after which the reaction mixture is acidified by 1M HCl. The mixture is extracted with EtOAc then washed with brine. The organic layer is dried over Na$_2$SO$_4$ and concentrated. The residue is purified by p-HPLC to give A-5.

To a suspension of A-5 (500 mg, 1.61 mmol) in DCM (20 mL) is added oxalyl chloride (0.82 mL, 9.64 mmol) and followed by DMF (0.15 mL). The reaction mixture is stirred at r.t. overnight. More oxalyl chloride (0.408 mL, 4.82 mmol) and DMF (0.05 mL) are added and the reaction mixture is stirred at RT for 1 hour. The reaction mixture is concentrated in vacuo then diluted with DCM and washed with sat. NaHCO$_3$ aqueous solution, dried over Na$_2$SO$_4$, filtered and concentrated to yield crude A-6 which is used directly in the next step.

To a stirred suspension of A-6 (530 mg, 1.61 mmol) in DMF (6 mL) is added DIEA (0.7 mL, 4.02 mmol), followed by AH (456 mg, 1.93 mmol). The reaction is allowed to stir for 1 h at rt. The reaction is quenched with water then extracted with EtOAc twice. The organics are combined and washed with brine, dried over Na$_2$SO$_4$, filtered and concentrated. The residue is purified by SiO$_2$ flash chromatography to yield intermediate A. MS (ES+): m/z 493.2/495.2 [M+H]$^+$.

Method 2:
Synthesis of Intermediate B

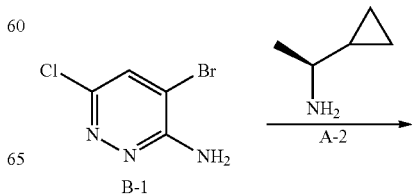

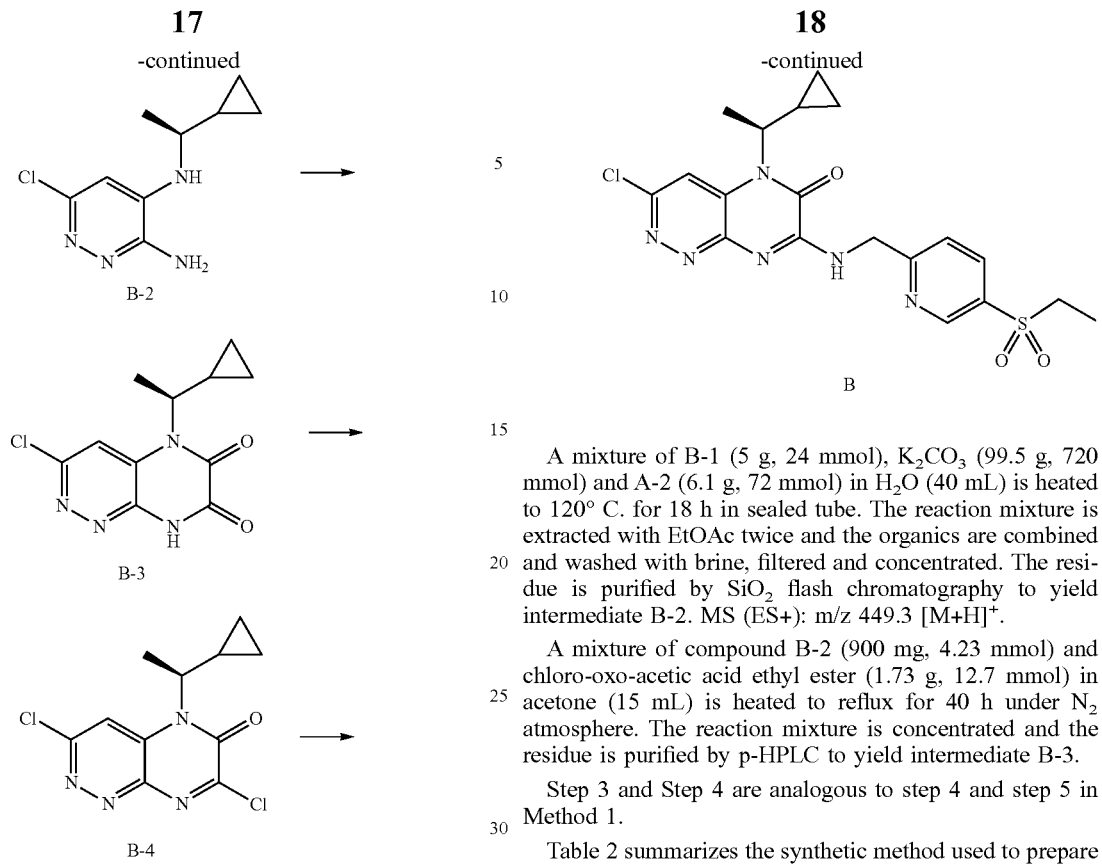

A mixture of B-1 (5 g, 24 mmol), K$_2$CO$_3$ (99.5 g, 720 mmol) and A-2 (6.1 g, 72 mmol) in H$_2$O (40 mL) is heated to 120° C. for 18 h in sealed tube. The reaction mixture is extracted with EtOAc twice and the organics are combined and washed with brine, filtered and concentrated. The residue is purified by SiO$_2$ flash chromatography to yield intermediate B-2. MS (ES+): m/z 449.3 [M+H]$^+$.

A mixture of compound B-2 (900 mg, 4.23 mmol) and chloro-oxo-acetic acid ethyl ester (1.73 g, 12.7 mmol) in acetone (15 mL) is heated to reflux for 40 h under N$_2$ atmosphere. The reaction mixture is concentrated and the residue is purified by p-HPLC to yield intermediate B-3.

Step 3 and Step 4 are analogous to step 4 and step 5 in Method 1.

Table 2 summarizes the synthetic method used to prepare intermediates B-F and the m/z found for each intermediate.

TABLE 2

| Intermediate | Structure | Synthetic Method | m/z [M + H]$^+$ |
|---|---|---|---|
| C | 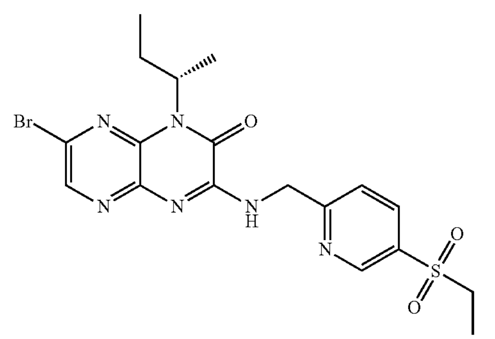 [SMILES: CC[C@H](C)n1c(=O)c(NCc2ccc(S(=O)(=O)CC)cn2)nc2ncc(Br)nc21] | 1 | 481.3/483.2 |
| D | 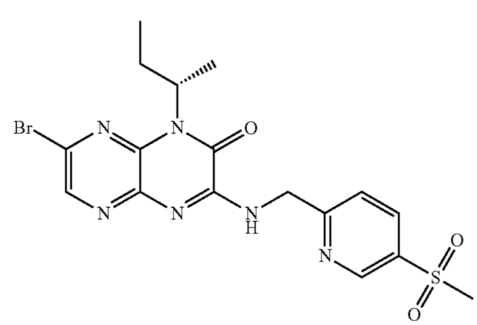 [SMILES: CC[C@H](C)n1c(=O)c(NCc2ccc(S(C)(=O)=O)cn2)nc2ncc(Br)nc21] | 1 | 467.2/469.2 |

TABLE 2-continued

| Intermediate | Structure | Synthetic Method | m/z [M + H]+ |
|---|---|---|---|
| E | 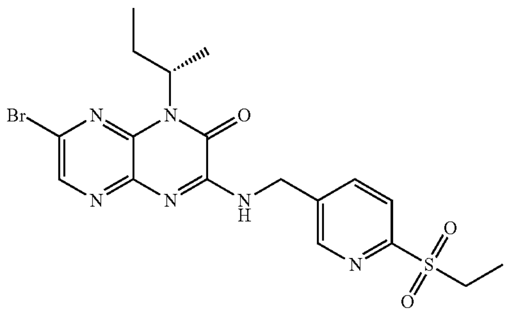 [SMILES: CC[C@H](C)n1c(=O)c(NCc2ccc(S(=O)(=O)CC)nc2)nc2ncc(Br)nc21] | 1 | 481.3/483.3 |
| F | 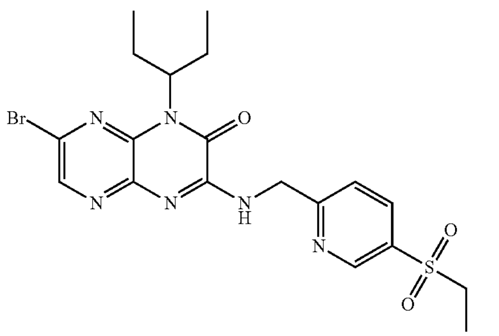 [SMILES: CCC(CC)n1c(=O)c(NCc2ccc(S(=O)(=O)CC)cn2)nc2ncc(Br)nc21] | 1 | 495.0/497.0 |
| G | 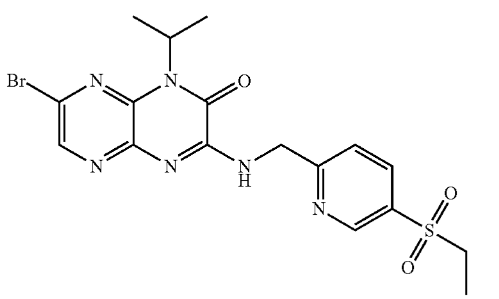 [SMILES: CCS(=O)(=O)c1ccc(CNc2nc3ncc(Br)nc3n(C(C)C)c2=O)nc1] | 1* | 467.1/469.1 |
| B | 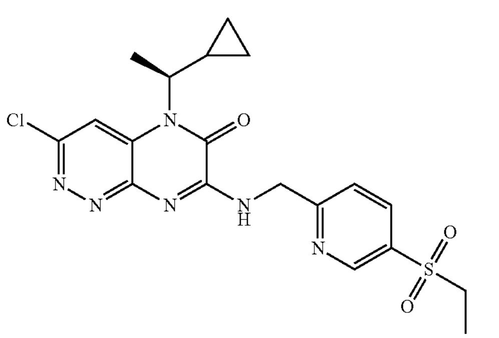 [SMILES: CCS(=O)(=O)c1ccc(CNc2nc3nnc(Cl)cc3n([C@@H](C)C3CC3)c2=O)nc1] | 2 | 449.3 |

*: first step using 10 equ. of diisopropylamine (no K₂CO₃ added).

Method 3:
Synthesis of Intermediate AB

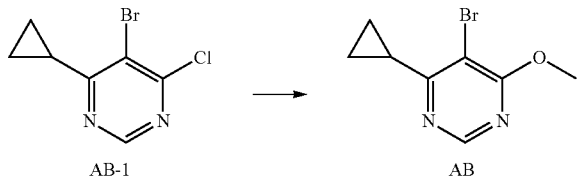

To a solution of AB-1 (300 mg, 1.29 mmol) in anhydrous MeOH (15 mL) is added NaOMe (208 mg, 3.86 mmol). The mixture is stirred at rt for 1 h. The solution is filtered and concentrated. The residue is purified by SiO$_2$ flash chromatography to yield intermediate AB. MS (ES+): m/z 230.8 [M+H]$^+$.

Method 4:
Synthesis of Intermediate AC

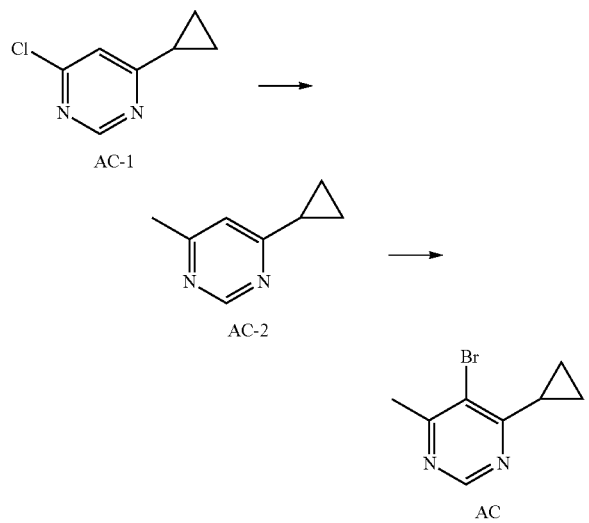

To a solution of AC-1 (320 mg, 2.07 mmol), 2,4,6-trimethyl-1,3,5,2,4,6-trioxatriborinane (520 mg, 4.14 mmol), and aq Na$_2$CO$_3$ (2M, 3.1 mL, 6.21 mmol) in dioxane (10 mL) is added dichloropalladium 4-di-tert-butylphosphanyl-N,N-dimethyl-aniline (73 mg, 0.10 mmol). The mixture is heated to 130° C. for 40 min in a microwave reactor. The mixture is diluted with MeOH (5 mL), filtered and concentrated. The residue is purified by SiO$_2$ flash chromatography to yield AC-2.

To a solution of AC-2 (363 mg, 2.71 mmol) in EtOH (10 mL) at −10° C. is added Br$_2$ (432 mg, 2.71 mmol). The reaction mixture is stirred at rt for 18 h. The solution is concentrated and the residue is purified by SiO$_2$ flash chromatography to yield intermediate AC. MS (ES+): m/z 214.3 [M+H]$^+$.

Method 5:
A. Synthesis of Intermediate AD

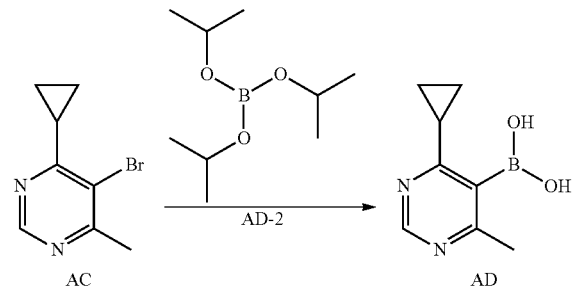

To a solution of AC (20 g, 93.86 mmol) in toluene (200 mL) and THF (50 mL) under Ar is added triisopropyl borate (28.2 mL, 122.02 mmol) and the resulting mixture is cooled to −74° C. n-BuLi (2.7 M in hexanes, 56.7 mL, 150.18 mmol) is added dropwise through an addition funnel over 1 h. After the addition, the reaction mixture is stirred at −74° C. for 5 min then quenched with 1N HCl aqu. solution (85 mL, 255.31 mmol). The mixture is slowly warmed up to room temperature then the layers are separated. To the stirring aqu. solution is added NaHCO$_3$ solid (10 g, 119.03 mmol). The product is collected by filtration.give additional intermediate AD. MS (ES+): m/z 178.3 [M+H]$^+$.

B. Synthesis of intermediate AE

Intermediate AE is synthesized in a fashion analogous to Intermediate AD.

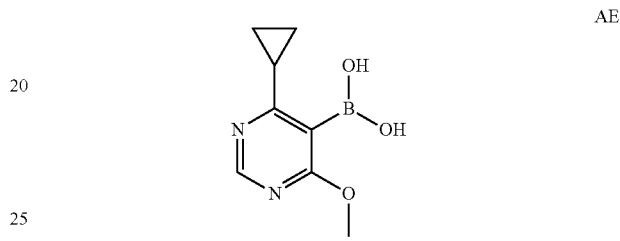

Method 6:
Synthesis of Intermediate AF

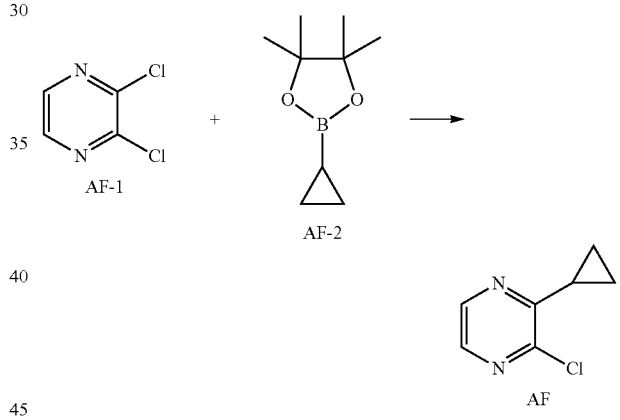

A mixture of AF-1 (400 mg, 2.69 mmol), AF-2 (451 mg, 2.69 mmol), Reider's catalyst (190 mg, 0.29 mmol) and 2M Na$_2$CO$_3$ aqueous solution (4 mL) in dioxane (8 mL) is purged with Ar then heated at 80° C. for 5 h. The reaction mixture is quenched with water then extracted with EtOAc twice. The organics are combined and washed with brine, dried over Na$_2$SO$_4$, filtered and concentrated. The residue is purified by SiO$_2$ flash chromatography to yield intermediate AF. MS (ES+): m/z 155.0 [M+H]$^+$.

Method 7:
Synthesis of Intermediate AG

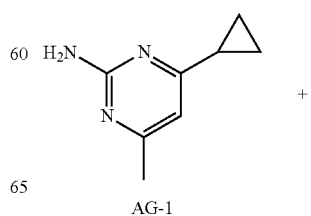

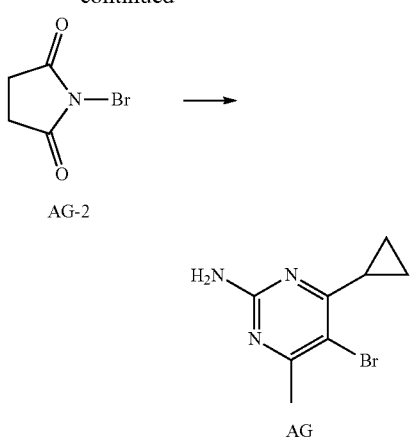

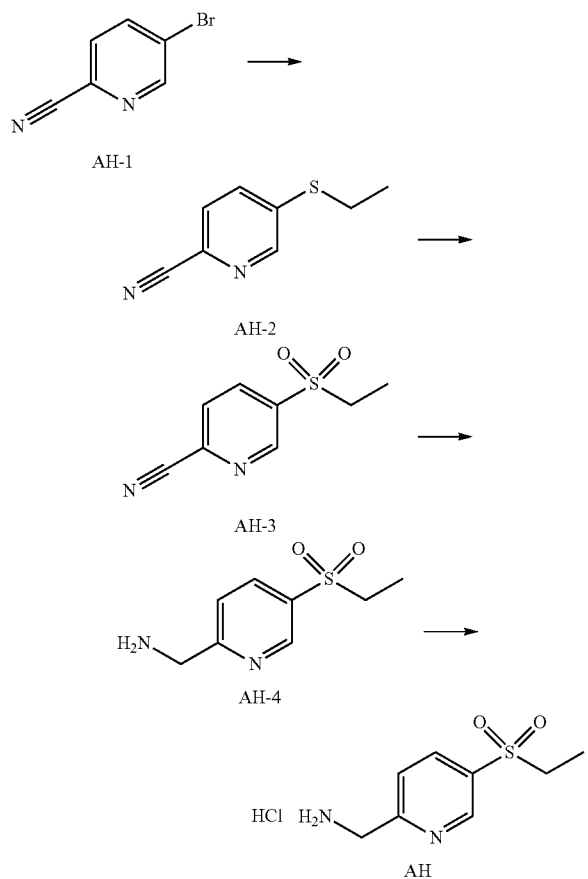

To a suspension of AG-1 (2 g, 13.41 mmol) in CH₃CN (50 mL) is added AG-2 (2.62 g, 14.75 mmol) and the reaction mixture is stirred at room temperature for 20 min and then filtered to yield intermediate AG. MS (ES+): m/z 229.7 [M+H]⁺.

Method 8:

Synthesis of Intermediate AH

A mixture of AH-1 (8.0 g, 43.96 mmol), K₂CO₃ (7.88 g, 57.1 mmol) and sodium ethanethiolate (4.06 g, 48.3 mmol) in NMP (60.0 mL) under N₂ is stirred at rt for 18 h. The reaction mixture is poured into H₂O and filtered. The solids are washed with H₂O and dried under vacuum to yield AH-2.

To a suspension of AH-2 (6.0 g, 36.6 mmol) in AcOH (2.63 g, 43.8 mmol) is added a solution of KMnO₄ (5.78 g, 36.6 mmol) in H₂O (20.0 mL) dropwise. The reaction mixture is stirred at rt for 15 h. The mixture is diluted with water and extracted with EtOAc. The organic layer is dried (Na₂SO₄), decanted and concentrated. The resulting residue is purified by SiO₂ flash chromatography to yield AH-3.

A solution of AH-3 (3.3 g, 16.8 mmol) and Pd/C (500 mg, 10% on carbon catalyst) in MeOH (30 mL) is stirred at rt under H₂ (50 psi) for 8 h. The vessel is purged with N₂, filtered and the filtrate concentrated to yield AH-4.

To a stirred solution of AH-4 (2.5 g, 12.5 mmol) in EtOAc (30 mL) is added HCl in EtOAc (2N, 20.0 mL). The solution is stirred at rt for 5 h and then filtered to yield intermediate AH. MS (ES+): m/z 201.2 [M+H]⁺.

Method 9:

Synthesis of Intermediate AI

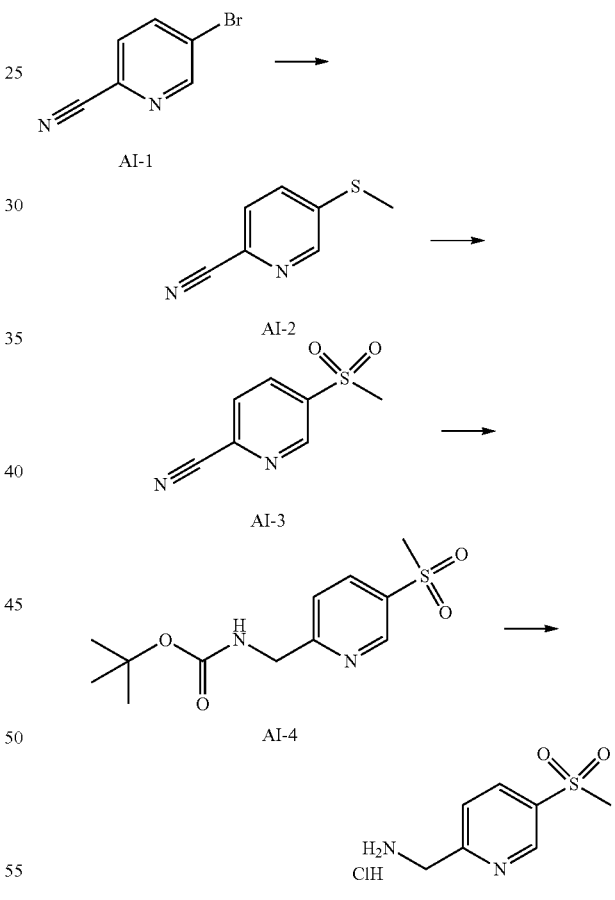

To a solution of AI-1 (82.0 g, 448 mmol) in ACN (1.0 L) is added sodium t-butoxide (64.5 g). The mixture is cooled to 0° C. and sodium methanethiolate (172.5 g, 20% in H₂O) is added dropwise. The reaction mixture is then allowed to stir at rt for 16 h. Water (800 mL) is added and the mixture is extracted with DCM. The combined organic phases are washed with brine, dried (Na₂SO₄) and concentrated. The residue is purified by SiO₂ flash chromatography to yield AI-2.

To a suspension of AI-2 (51.5 g, 343 mmol) in AcOH (500 mL) is added a solution of KMnO₄ (59.7 g, 36.6 mmol) in H₂O (500.0 mL) dropwise at 5° C. The reaction mixture is then stirred at rt for 1 h. The mixture is extracted with EtOAc, washed with aq. NaHCO₃, dried (Na₂SO₄) and concentrated. The resulting residue is purified by recrystallization to yield AI-3.

To a solution of AI-3 (15.0 g, 82 mmol) in MeOH (200 mL) is added RaNi (10.0 g), TEA (34.4 mL) and Boc₂O (17.8 g). The mixture is stirred at rt under H₂ (50 psi) for 12 h. The vessel is purged with N₂, filtered and the filtrate concentrated. The residue is purified by SiO₂ flash chromatography to yield AI-4.

A solution of AI-4 (30.0 g, 105 mmol) in HCl in MeOH (500 mL) is stirred at rt for 12 h. The mixture is concentrated and recrystallized to yield intermediate AI. MS (ES+): m/z 187 [M+H]⁺.

Method 10:

Synthesis of Intermediate AJ

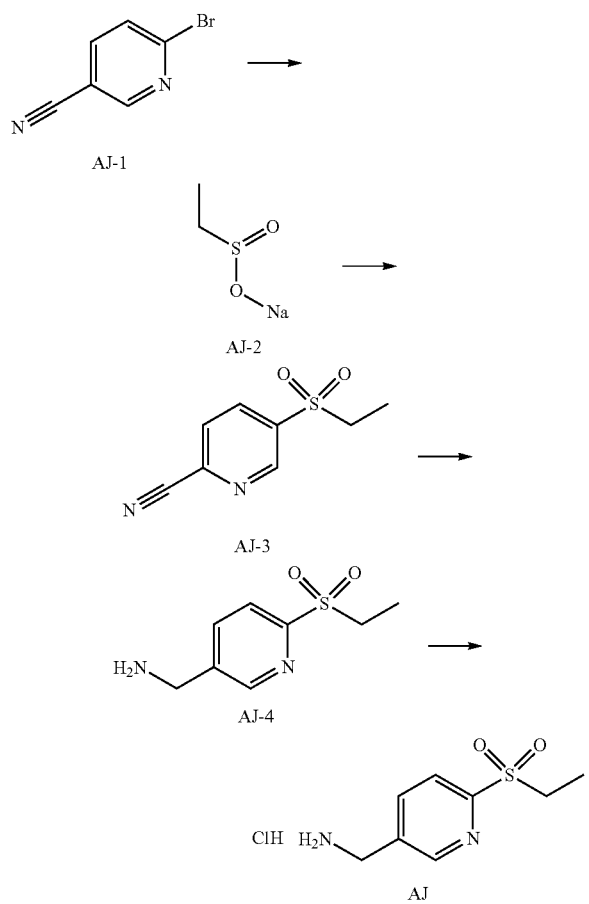

To a mixture of AJ-1 (10.0 g, 55 mmol), N,N-dimethylethane-1,2-diamine (0.96 g, 11 mmol) and copper(II) trifluoromethanesulfonate (1.98, 5 mmol) in DMSO (100 mL) is added AJ-2 (8.27 g, 98 mmol) at rt. The mixture is then heated to 120° C. for 30 min, quenched with H₂O and extracted with EtOAc. The organic layer is dried, concentrated and purified by SiO₂ flash chromatography to yield AJ-3.

A mixture of AJ-3 (32.3 g, 165 mmol) and Pd (3.50 g, 33 mmol) in NH₄OH (30 mL)/EtOH (200 mL) is stirred at rt under H₂ (15 psi) for 15 h. The mixture is filtered, concentrated and purified by SiO₂ flash chromatography to yield AJ-4.

To a stirred solution of AJ-4 (17.5 g, 87 mmol) in EtOH (100 mL) is added HCl in EtOH (100 mL). The solution is stirred at rt for 3 h and then concentrated and recrystallized to yield intermediate AJ. MS (ES+): m/z 201 [M+H]⁺.

Method 11:

Synthesis of Example 4.

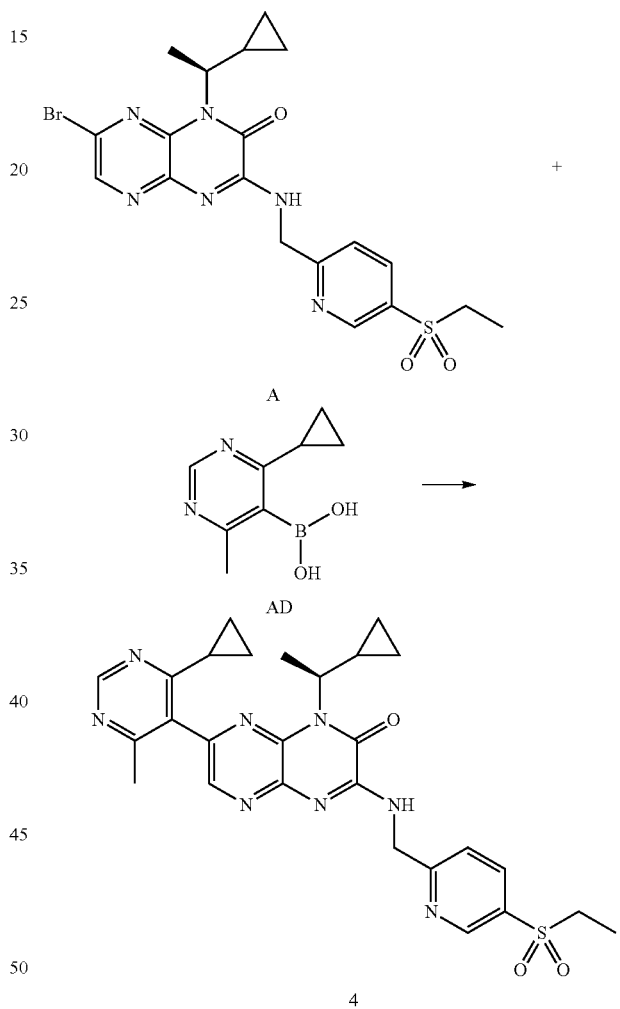

A mixture of A (127 mg, 0.26 mmol), intermediate AD (69 mg, 0.39 mmol), K₃PO₄ (109 mg, 0.52 mmol), in 1,4-dioxane (2.7 mL) and H₂O (0.31 mL) is purged with argon, and then Pd(dppf)Cl₂ (21 mg, 0.026 mmol) is added. The mixture is degassed with N₂, sealed then heated at 100° C. for 18 h. After cooling to rt, the mixture is diluted with water and extracted with EtOAc twice. The combined organic phase is dried (Na₂SO₄), filtered and concentrated. The resulting residue is purified by SiO₂ flash chromatography followed by reverse phase HPLC to yield Example 4. MS (ES+): m/z 547.3 [M+H]⁺.

Examples 3, 7, 8, 9, 10 and 11 are synthesized in an analogous fashion using the appropriate intermediates listed in Table 2.

Method 12:
Synthesis of Example 5

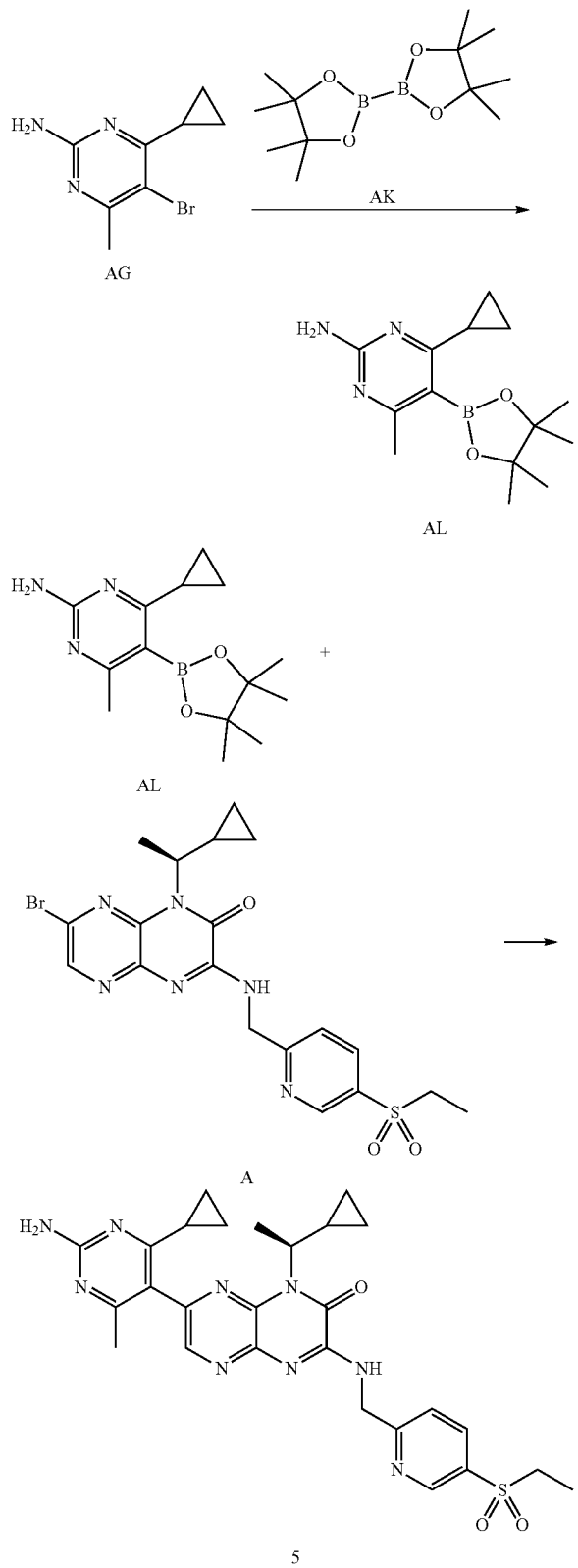

mixture solvents (2 mL, toluene/DME/EtOH/H$_2$O 10:6:3:1) in a vial is degassed with N$_2$ then added Pd(dppf)Cl$_2$ (43 mg, 0.053 mmol), purged with Ar, sealed then heated at 90° C. in microwave reactor for 1 h to yield crude AL which is used directly in the next step.

To a mixture of A (124 mg, 0.25 mmol) and Reider's catalyst (36 mg, 0.05 mmol) in DMF (3 mL) and 2N Na$_2$CO$_3$ aqu. solution (2.5 mL) is added AL. The vial is purged with Ar then heated at 110° C. for 30 min. The reaction mixture is quenched with water then extracted with EtOAc twice. The organics are combined and washed with brine, dried over Na$_2$SO$_4$, filtered and concentrated. The residue is purified by SiO$_2$ flash chromatography first then by p-HPLC to yield Example 5. MS (ES+): m/z 562.5 [M+H]$^+$.

Examples 1, 2 and 6 are synthesized in an analogous fashion using the appropriate intermediates listed in Table 2.

Method 13:
Synthesis of Example 12

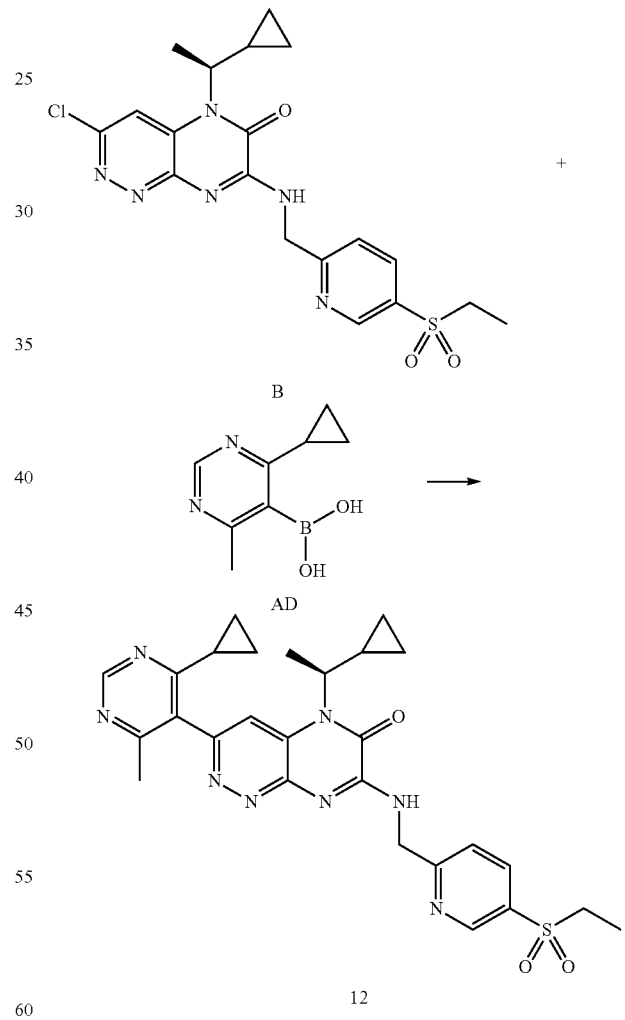

A mixture of AG (120 mg, 0.53 mmol), AK (223 mg, 0.88 mmol) and potassium acetate (129 mg, 1.32 mmol) in A mixture of B (59 mg, 0.13 mmol), AD (35 mg, 0.20 mmol) and K$_3$PO$_4$ (55.4 mg, 0.26 mmol) in dioxane (2 mL) and water (0.2 mL) is degassed with N$_2$. XPhos Pd G2 (10.3 mg, 0.013 mmol) is then added, the mixture is degassed with N$_2$, sealed and heated at 100° C. in a microwave reactor for 30 min. The reaction mixture is quenched with water then extracted with EtOAc twice. The organics are combined and washed with brine, dried over $Na_2SO_4$, filtered and concentrated. The residue is purified by $SiO_2$ flash chromatography then further purified by preparative thin layer chromatography to yield Example 12. MS (ES+): m/z 547.5 $[M+H]^+$.

Biological Activity

The compounds of the present invention have activity as modulators of RORγ (retinoid acid receptor-related orphan receptor γ).

Reporter Gene Assay (RGA)

A nuclear receptor transactivation assay is performed to quantitate the ability of test compounds to inhibit RORγ transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Gal4DBD hRORC LBD1-3). The positive control is co-transiently transfected with both plasmids, and the negative control contains the pGL4.3 promoter sequence. Assays are assembled in 384 well plates where transiently transfected cells and test compound at varying concentrations are incubated for 20-24 h. The next day, assays plates are taken out and equilibrated at RT for 20-30 minutes. Bright-Glo™ Luciferase Assay System is used to detect Luciferase production. After addition of Bright GLO detection reagent, the plates are incubated at RT for 20 minutes. The plates are read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, 1×Penicillin-Streptomycin-Gibco #15140

Compound Dilution Buffer:
1× HBSS-Invitrogen #14025126

Assay Plates: Greiner #781080-020

Bright Glo Luciferase Assay System: Promega #E2620

Thaw lysis buffer provided in kit, add 100 mL lysis buffer to substrate powder.

Table 3 presents the results obtained when the compounds of the present invention were tested in the above assay, demonstrating their activity as modulators of RORγ.

TABLE 3

| Example | RGA $IC_{50}$ (nM) |
| --- | --- |
| 1 | 557 |
| 2 | 1200 |
| 3 | 149 |
| 4 | 269 |
| 5 | 274 |
| 6 | 454 |
| 7 | 210 |
| 8 | 338 |
| 9 | 1327 |
| 10 | 2735 |
| 11 | 5700 |
| 12 | 2900 |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORγ.

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of RORγ modulators is of therapeutic benefit, including but not limited to the treatment of autoimmune or allergic disorders.

Such disorders that may be treated by the compounds of the invention include for example: rheumatoid arthritis, psoriasis, systemic lupus erythromatosis, lupus nephritis, systemic sclerosis, vasculitis, scleroderma, asthma, allergic rhinitis, allergic eczema, multiple sclerosis, juvenile rheumatoid arthritis, juvenile idiopathic arthritis, type I diabetes, Crohn's disease, ulcerative colitis, graft versus host disease, psoriatic arthritis, reactive arthritis, ankylosing spondylitis, atherosclerosis, uveitis and non-radiographic spondyloarthropathy.

For treatment of the above-described diseases and conditions, a therapeutically effective dose will generally be in the range of approximately 0.01 mg to about 10 mg/kg of body weight per dosage of a compound of the invention; preferably, from about 0.1 mg to about 5 mg/kg of body weight per dosage. For example, for administration to a 70 kg person, the dosage range would be approximately 0.7 mg to about 750 mg per dosage of a compound of the invention, preferably from about 7.0 mg to about 350 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and generally comprise at least one compound of the invention and at least one pharmaceutically acceptable carrier. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

All patent and non-patent documents or literature cited in this application are herein incorporated by reference in their entirety.

What is claimed is:

1. A compound of formula (I):

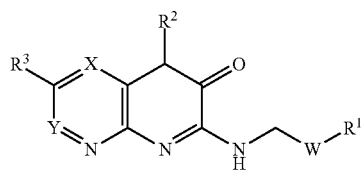

(I)

or a pharmaceutically acceptable salt thereof, wherein:
(i) X is N; and
  Y is CH; or
(ii) X is CH; and
  Y is N;
$R^1$ is $S(O)_nR^7$, $S(O)NHR^7$, or $S(O)_nNR^8R^9$;
$R^2$ is $C_{1-6}$ alkyl, wherein the $C_{1-6}$ alkyl is optionally substituted with 1 or 2 substituents independently selected from the group consisting of halogen, CN, $CF_3$, and $C_{3-6}$ cycloalkyl;
$R^3$ is:

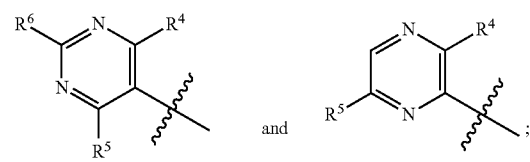

$R^4$ is $C_{1-3}$ alkyl, $OCH_3$, or cyclopropyl;
$R^5$ is $C_{1-3}$ alkyl, $OCH_3$, or cyclopropyl;
$R^6$ is H, $C_{1-3}$ alkyl, $NH_2$, $OCH_3$, or cyclopropyl;
$R^7$ is $C_{1-3}$ alkyl;
$R^8$ is H;
$R^9$ is H;
W is phenyl, pyridinyl, pyrimidinyl, or pyrizinyl; and
n is 1 or 2.

2. The compound according to claim 1, or a pharmaceutically acceptable salt thereof, wherein:
X is N; and
Y is CH.

3. The compound according to claim 1, or a pharmaceutically acceptable salt thereof, wherein $R^3$ is:

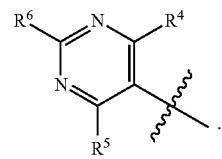

4. The compound according to claim 1, or a pharmaceutically acceptable salt thereof, wherein:
$R^1$ is $S(O)_nR^7$;
$R^2$ is $C_{1-6}$ alkyl, wherein the $C_{1-6}$ alkyl is optionally substituted with 1 or 2 substituents independently selected from the group consisting of CN, $CF_3$, and cyclopropyl;
$R^6$ is H or $NH_2$;
W is phenyl, pyridin-2-yl, pyridin-3-yl, or pyrimidin-2-yl; and
n is 2.

5. The compound according to claim 1, or a pharmaceutically acceptable salt thereof, wherein:
X is N;
Y is CH;
$R^1$ is $S(O)_nR^7$;
$R^2$ is $C_{1-5}$ alkyl, wherein the $C_{1-5}$ alkyl is optionally substituted with 1 cyclopropyl substituent;
$R^3$ is:

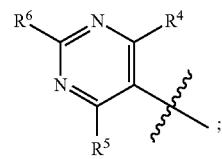

$R^6$ is H;
W is pyridin-2-yl or pyridin-3-yl; and
n is 2.

6. The compound according to claim 1, wherein the compound is selected from the group consisting of:

1

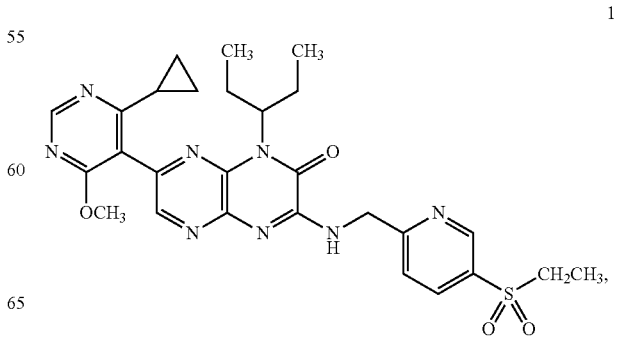

2
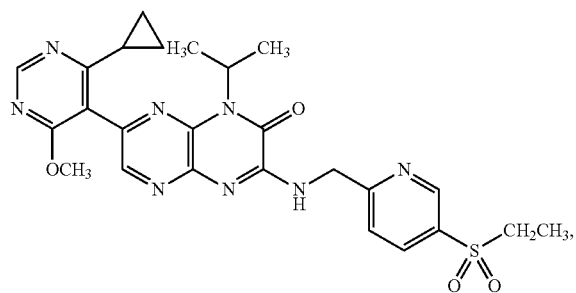
3
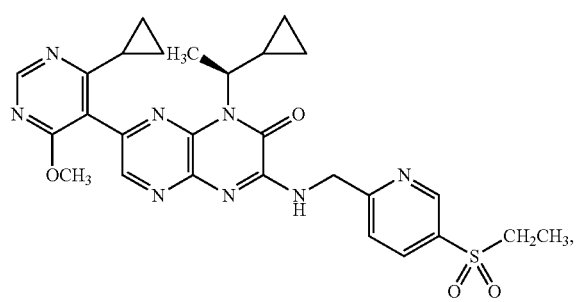
4
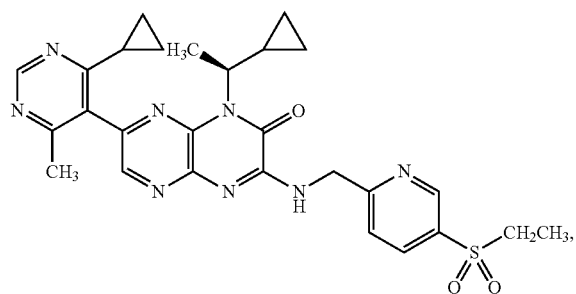
5
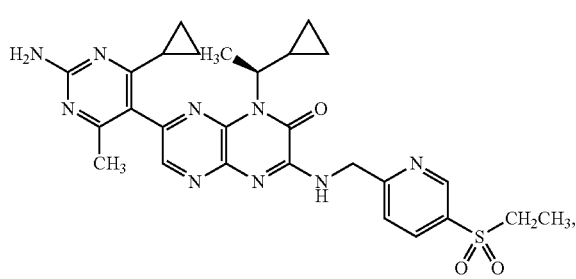
6
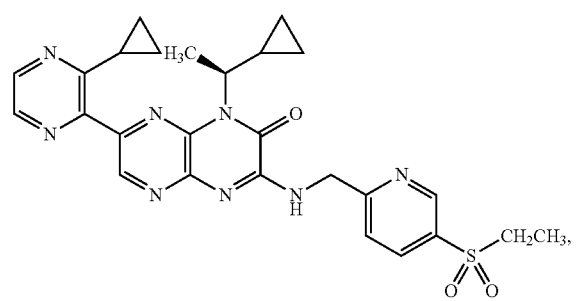
7
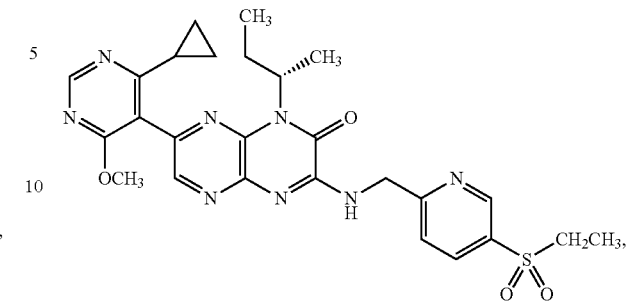
8
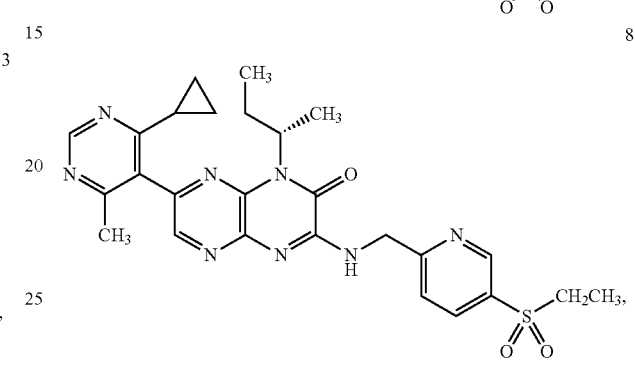
9
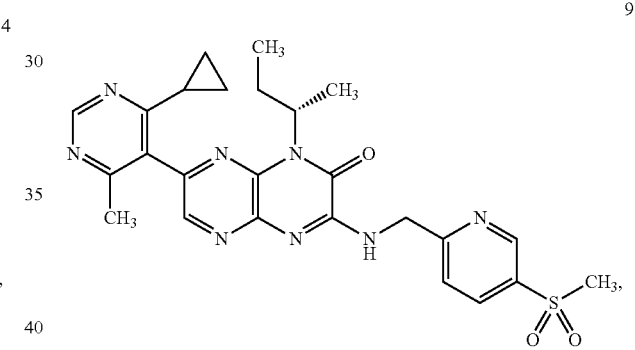
10
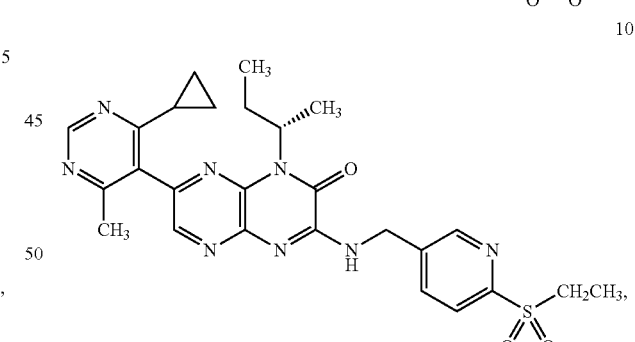
11
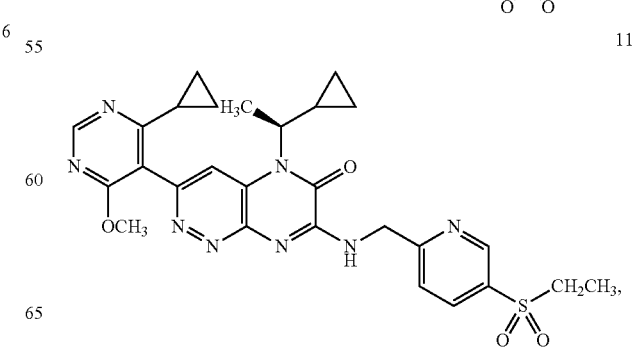

-continued and

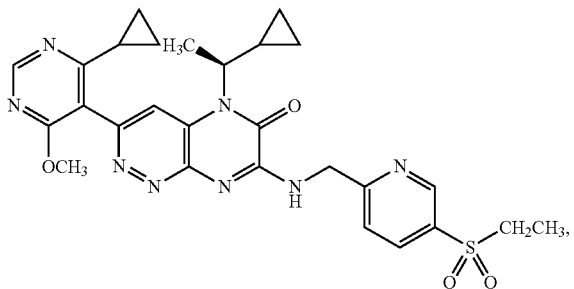

or a pharmaceutically acceptable salt thereof.

7. A pharmaceutical composition comprising a pharmaceutically acceptable excipient or carrier and the compound according to claim 1, or a pharmaceutically acceptable salt thereof.

8. A method for inhibiting retinoic acid receptor related orphan receptor gamma activity in a patient, wherein the method comprises administering to the patient in need thereof a therapeutically effective amount of the compound according to claim 1, or a pharmaceutically acceptable salt thereof.

9. The method according to claim 8, wherein the patient has an autoimmune disease or allergic disorder selected from the group consisting of allergic eczema, allergic rhinitis, ankylosing spondylitis, asthma, Crohn's disease, graft versus host disease, inflammatory bowel disease, juvenile idiopathic arthritis, lupus nephritis, multiple sclerosis, psoriasis, psoriatic arthritis, reactive arthritis, rheumatoid arthritis, scleroderma, systemic lupus erythromatosis, type 1 diabetes, ulcerative colitis, and uveitis.

10. The method according to claim 9, wherein the rheumatoid arthritis is juvenile rheumatoid arthritis.

* * * * *